United States Patent [19]

Dorward et al.

[11] Patent Number: 5,308,753
[45] Date of Patent: May 3, 1994

[54] METHODS FOR PURIFYING AND DETECTING IGM ANTIBODIES

[75] Inventors: David W. Dorward, Hamilton, Mont.; Edward D. Huguenel, Guilford; Gary Davis, Milford, both of Conn.; Claude F. Garon, Hamilton, Mont.

[73] Assignee: The Government of the United States of America as represented by the Secretary of the Department of Health and Human Services, Md.

[21] Appl. No.: 837,892

[22] Filed: Feb. 20, 1992

[51] Int. Cl.$^5$ .................. G01N 33/53; C07K 3/18
[52] U.S. Cl. .................. 435/7.32; 435/7.92; 435/971; 436/513; 436/518; 436/536; 436/538; 530/413; 530/825; 530/863
[58] Field of Search .......... 435/7.32, 7.92, 820, 435/961, 971; 436/513, 518, 536, 538, 541, 824; 530/388.4, 389.5, 413, 825, 863

[56] References Cited

U.S. PATENT DOCUMENTS 5,077,391 12/1991 Raison et al. ............... 530/413
5,187,065 2/1993 Schutzer ..................... 435/7.32

FOREIGN PATENT DOCUMENTS

90/04411 5/1991 World Int. Prop. O. .

OTHER PUBLICATIONS

Craft et al., "Antigens of *Borvelia burgdorferi* recognized during Lyme Disease", J. Clin. Invest., 78:934–939 (Oct. 1986).
Benach et al., "A Murine IgM Monoclonal Antibody Binds an Antigenic Determinant in Outer Surface Protein A, An Immunodominant Basic Protein of the Lyme Disease Spirochete", J. Immunol., 140:265-272 (Jan. 1988).
Dorward et al., "Immune Capture and Detection of *Borrelia burgdorferi* Antigens in Urine, Blood or Tissues from Infected Ticks, Mice, Dogs and Humans", J. Clin. Microbiol., 29(6):1162-1170 (Jun. 1991).
Hanson et al., "Measurement of Antibodies to *Borrelia burgdorferi* Flagellum Improves Serodiagnosis in Lyme Disease", J. Clin. Microbiol., 26(2):338-346 (Feb. 1988).

*Primary Examiner*—Esther L. Kepplinger
*Assistant Examiner*—Carol E. Bidwell
*Attorney, Agent, or Firm*—Morgan & Finnegan

[57] ABSTRACT

Methods for purifying and detecting IgM antibodies employ binding substances which are *Borellia burgdorferi* cells, or cellular or extracellular components obtained or derived therefrom and which bind to this class of antibodies. The binding substances may be attached to a solid substrate and then the substrate contacted with a solution containing IgM antibodies under conditions such that the antibodies bind to the binding substance on the substrate. The substrate is then contacted with a solution that releases the IgM antibodies from the substrate and the antibodies are recovered or detected. Applications of these methods include, for example, assays for diagnosing diseases which elicit primary and/or secondary IgM antibody-mediated immunity.

15 Claims, 6 Drawing Sheets

FIG. 3C
CBB

FIG. 3D
Immunoblots

FIG. 3E
Immunoblots

METHODS FOR PURIFYING AND DETECTING IGM ANTIBODIES

BACKGROUND OF THE INVENTION

1. Field of the Invention

The present invention generally relates to methods and kits for isolating and/or detecting IgM antibodies by employing binding substances which are *Borrellia burgdorferi* cells, or cellular or extracellular components obtained or derived therefrom, as well as to related applications therefor.

2. Description of Related Art

Infection with the spirochete *Borrelia burgdorferi* causes the acute and chronic manifestations of Lyme borreliosis (Burgdorfer, W., A. G. Barbour, S. F. Hayes, J. L. Benach, and J. P. Davis. 1982. Lyme disease—a tick-borne spirochetosis? *Science* 216:1317-1319). Despite considerable work on humoral and cell-mediated responses to infection, which has recently been reviewed (Steere, A. C. 1989. Lyme Disease. *New. Engl. J. Med.* 321:586-596. Szczepanski, A., and J. L. Benach. 1991. Lyme borreliosis: host responses to *Borrellia burgdorferi*. *Microbiol. Rev.* 55:21-34), the pathogenic mechanisms that contribute to chronic disease induced by this spirochete remain obscure. It is evident that *B. burgdorferi* is susceptible to complement-mediated cytolysis and phagocytic clearance (Steere, 1989, pp. 586-596; Szczepanski et al., 1991, pp. 21-34). Furthermore, most, if not all, uncompromised mammalian hosts develop a significant humoral response to infection (Steere, 1989, pp. 586-596; Szczepanski et al., 1991, pp. 21-34). However, the persistent infections documented in humans and animal models indicate that immune clearance is either rare or non-existent (Steere, 1989, pp. 586-596; Szczepanski et al., 1991, pp. 21-34). Several studies have demonstrated passive protection by antibodies, and active protection by vaccination in animal models (Steere, 1989, pp. 586-596; Szczepanski et al., 1991, pp. 21-34). Such protection is apparently transient, requiring immunization during a limited period prior to infectious challenge.

Little evidence suggests that antigenic variation contributes significantly to transient protection and persistent infection (Steere, 1989, pp. 586-596; Szczepanski et al., 1991, pp. 21-34). Although antigenic differences among various isolates have been documented (Barbour, A. G., S. L. Tessier, and S. F. Hayes. 1984. Variation in a major surface protein of Lyme Disease Spirochetes. *Infect. Immun.* 45:94-100; Schwan, T. G. and W. Burgdorfer. 1987. Antigenic changes of *Borrelia burgdorferi* as a result of in vitro cultivation. *J. Infect. Dis.* 156:852-853; Steere, 1989, pp. 586-596; Szczepanski et al., 1991, pp. 21-34), dramatic antigenic changes during chronic infection have not been reported. Furthermore, no evidence for antigenic shifts or gene rearrangements in *B. burgdorferi*, similar to those believed to function as immune evasion mechanisms in the relapsing fever agent *B. hermsii* (Barbour, A. H., C. J. Carter, N. Burman, C. S. Freitag, C. F. Garon, and S. Bergström. 1991. Tandem insertion sequence-like elements define the expression sites for variable antigen genes of *Borrelia hermsii*. Infect. Immun. 59:390-397), has been described. Such observations have led to suggestions that *B. burgdorferi* persistent infections are maintained by spirochetes that become sequestered from immune effectors.

Recent studies using an antigen capture and detection assay demonstrated aggregates of extracellular *B. burgdorferi* antigens in fluids and tissues from infected arthropod and mammalian hosts (Dorward, D. W., T. G. Schwan, C. F. Garon. 1991. Immune capture and detection of extracellular *B. burgdorferi* antigens in fluids or tissues of ticks, mice, dogs, and humans. *J. Clin. Microbiol.* 29:1162-1171). The assay system utilized polyclonal F(ab')$_2$ fragments generated against extracellular vesicle concentrates to capture antigens, which were subsequently labeled and detected using polyclonal IgG antibodies specific for *B. burgdorferi*. These antibodies were raised against an 83 kDa major extracellular protein (MEP) band, but reacted primarily with OspA and OspB from geographically diverse isolates. The assay enabled consistent detection of the aggregates in samples from which spirochetes were rarely observed, suggesting tat the aggregates were constantly circulating, or that the aggregates were deposited by motile spirochetes and persisted in situ. The study also showed that the antigen aggregates could be recovered from culture supernatants along with extracellular membrane vesicles, and that the aggregates may be derived from s-layer material. However, the apparent relationship between the Osp proteins and the 83 kDa band was not pursued beyond demonstrating the reactivity of anti-MEP IgG antibodies (Dorward et al., 1991, pp. 1162-1171).

IgG-binding proteins have conventionally been used to detect the presence of IgG antibodies in solutions, or on surfaces exposed to IgG antibodies by a variety of techniques. Techniques which are commonly used include: Enzyme-linked immunosorbent assay (ELISA), radioimmunoassay (RIA), immunoblot analysis, immunofluorescent assay (IFA), immunohistochemistry, immunoelectron microscopy (IEM), and immunoilluminescence. Each technique utilizes specific protein conjugates to visualize the binding of the protein conjugate to antibody molecules. Two types of proteins are typically used as conjugates. These are bacterial immunoglobulin binding proteins (Fc receptors) and mammalian antibodies directed against other antibodies. Although both types have unique advantages and disadvantages, bacterial proteins generally offer greater stability at less cost per application. Currently, only staphylococcal protein A, and streptococcal protein G, which exclusively bind to IgG antibody molecules are commonly used. A wide variety of enzyme-linked, radioactive, fluorescent, illuminescent, and metallocolloid conjugates of these proteins are commercially available. However, no IgM-specific bacterial protein conjugates have been developed. Therefore, it is desirable to develop an IgM-binding substance or protein which may be used to purify or detect IgM antibodies and which also may be employed in the above-noted application, for IgG-binding proteins.

SUMMARY OF THE INVENTION

Therefore, it is an object of the present invention to provide methods for purifying and/or detecting IgM antibodies.

It is a further object of the present invention to provide methods for purifying and/or detecting outer surface protein from the bacterium *B. burgdorferi*.

It is yet another object of the present invention to provide kits useful for conducting methods for purifying and/or detecting IgM antibodies and outer surface proteins from *B. burgdorferi*.

The foregoing objects and others are accomplished in accordance with the present invention by providing methods for purifying and/or detecting IgM antibodies which employ binding substances which are *B. burgdorferi* cells, or cellular or extracellular components obtained or derived therefrom that bind to this class of antibodies.

Further scope of the applicability of the present invention will become apparent from the detailed description and drawings provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention is further illustrated in the accompanying drawings wherein.

DETAILED DESCRIPTION OF THE INVENTION

The present invention is directed to methods and kits for purifying and/or detecting IgM antibodies, as well as to methods and kits for purifying and/or detecting outer surface proteins from *Borrelia burgdorferi* and other assays based on these methods. The embodiments of the present invention are based on the inventors' investigation of the interactions between (1) *B. burgdorferi* cells, or cellular or extracellular components obtained or derived therefrom, including outer surface proteins therefrom, and (2) non-Borrelia directed IgM antibodies.

In accordance with a first embodiment of the present invention, a method is provided for isolating or detecting IgM including the step of contacting a liquid mixture containing IgM with a binding substance including *B. burgdorferi* cells, or cellular or extracellular components obtained or derived therefrom under conditions favorable to binding of IgM to the binding substance. The complexes formed by the binding of IgM with the binding substance may then be separated from the remainder of the liquid mixture for isolation of IgM. The binding substance may be immobilized to a solid substrate and the solid substrate then separated from the remainder of the liquid mixture for isolation or detection. The separated solid substrate may be subjected to conditions which effect dissociation of the bound IgM. The complexes may also be detected in the liquid mixture. For this purpose, a label may be employed in association with the binding substance or in a labeled reagent that binds to the complexes subsequent to their formation. The binding substance may be an outer surface protein of *B. burgdorferi*, such as OspA or OspB.

In accordance with a second embodiment of the present invention, a method is provided for purifying IgM from a liquid mixture which includes (a) contacting the liquid mixture with an affinity substrate including a solid substrate to which is immobilized an outer surface protein of *B. burgdorferi*, wherein the contact is performed under conditions favorable to binding of IgM to the immobilized outer surface protein, (b) contacting the affinity substrate obtained from step (a) with a liquid capable of dissociating IgM from the immobilized outer surface protein, and (c) recovering the dissociated IgM.

In accordance with a third embodiment of the present invention, a method is provided for detecting IgM in a liquid mixture suspected to contain IgM, which includes (a) contacting the liquid mixture with an outer surface protein of *B. burgdorferi* under conditions favorable to binding of IgM to the outer surface protein, and (b) detecting complexes formed by binding of IgM with the outer surface protein. The complexes may be detected by employing an outer surface protein that is immobilized, contacting the complexes with a labeled reagent which binds with IgM and has a detectable label, and detecting the label. Alternatively, the complexes may be detected by employing outer surface protein hat is labeled with a detectable label, separating the labeled outer surface protein which becomes bound to IgM from that which remains unbound, and detecting the label in one of the separated species. The labeled outer surface protein which becomes bound to IgM may be separated by contacting the complexes with an immobilized form of a reagent that binds with IgM and then separating the immobilized reagent from the remaining mixture.

In accordance with a fourth embodiment of the present invention, a method is provided for the purification of an outer surface protein of *B. burgdorferi*, which includes the steps of (a) contacting the liquid mixture with an affinity substrate including a solid substrate to which is immobilized a moiety which binds to the outer surface protein, wherein the contact is performed under conditions favorable to binding of the outer surface protein to the immobilized moiety, (b) contacting the affinity substrate obtained from step (a) with a liquid capable of dissociating the outer surface protein from the immobilized moiety, and (c) recovering the dissociated outer surface protein of *B. burgdorferi*. The moiety which binds to the outer surface protein may be selected from among immunoglobulin of the IgM class, the heavy chain polypeptide of the immunoglobulin IgM class, the Fc portion of immunoglobulin of the IgM class, the oligosaccharide portion of immunoglobulin of the IgM class, and an oligosaccharide containing sialic acid.

In accordance with a fifth embodiment of the present invention, a kit for purifying or detecting IgM in a sample is provided which includes an affinity substrate constituting a solid substrate to which is immobilized a binding substance which constitutes *Borrelia burgdorferi* cells, or cellular or extracellular components obtained or derived therefrom, for receiving a sample solution suspected to contain IgM under conditions favorable to binding of IgM to the immobilized binding substance; and a container containing a solution capable of dissociating IgM from the affinity substrate such that the IgM is released for recovery or detection. The binding substance may be an outer surface protein from *B. burgdorferi*.

PREFERRED EMBODIMENTS

Detection of IgM Antibodies

The results of experiments conducted by the inventors indicate that binding substances constituting *B. burgdorferi* cells, or cellular or extracellular components obtained or derived therefrom, such as OspA and OspB proteins exported by *B. burgdorferi*, has a selective binding activity with IgM antibodies, independent of the antibody epitope (antigen recognition specificity). Such binding apparently does not occur between the binding substance or Osp proteins and other serum components. Thus, this IgM binding specificity can be employed for detecting and/or purifying IgM antibodies. Native or recombinant *B. burgdorferi* OspA protein is purified by previously published procedures (Dunn et al, "Outer surface protein A (OspA) from . . . ," *Protein Expression and Purification*, 1:159-168). The protein is then conjugated to a material that will enable visualization of the presence of the Osp protein. Commonly used conjugates include, but are not limited to, enzymes such as horseradish peroxidase, alkaline phosphatase, acid phosphatase, and luciferase, radioisotopes such as 125I, 35S, 14C, and 3H, fluorescent dyes such as fluorescein, and rhodamine, and colloidal gold particles. Effective procedures for such conjugations are generally conventional (Harlow et al, 1988, *Antibodies: a laboratory manual*, Cold Spring Harbor Haboratory, Cold Spring Harbor, N.Y.). The protein conjugate is stored in appropriate buffers until needed. Colloidal gold conjugates may be maintained in Tris-based stabilizing buffer, such as those described in Robinson et al, 1984, "Ultrastructural localization of specific . . . ," *Infect. Immun.* 46:361-366. For other conjugates, the buffer would typically be phosphate-buffered saline, pH 7.2 (PBS). However, physiological buffers such as Tris- or borate-buffered saline (TBS or BBS) in Ph ranging from 6.5 to 8.0, or non-saline buffers such as acetates, bicarbonates, or citrates within this Ph range may be utilized.

When needed to detect the presence of IgM antibodies in a preparation, the Osp protein conjugate may be first dilute in an appropriate buffer. The extent of dilution varies according to the conjugate and sensitivity required, and is normally determined empirically for a given conjugate preparation and detection method. Dilutions typically range from 1:10 to 1:10,000. After dilution the conjugate is incubated with a sample suspected of containing IgM antibodies. The incubation should proceed for about 15-60 minutes at room temperature, or about 4-16 hours at about 4° C., during which time from one to ten (optimally) Osp molecules will bind to any IgM antibodies present. Following incubation, the sample is washed twice for about 5-10 minutes each with dilution buffer or with buffer which is compatible with the visualization conditions (if different). The presence of bound Osp protein may then be detected or visualized by chromogenic assay, radioactivity, illuminescence, fluorescence, or electron density, as appropriate for the conjugate.

Purification of IgM Antibodies

Conjugates of Osp proteins may also be used to purify IgM antibodies by methods similar to those used for purification of IgG antibodies with protein A and protein G. Such affinity purification methods generally utilize insoluble or immobile protein conjugates to facilitate eventual separation of the antibody and the immunoglobulin-binding protein. A purification procedure for IgM antibodies using Osp protein conjugates may employ native or recombinant OspA protein which is purified as described above. The protein is then conjugated to an insoluble matrix by methods such as those described previously (Harlow et al, 1988, *Antibodies: a laboratory manual*. Cold Spring Harbor Laboratory, Cold Spring Harbor, N.Y.). Appropriate matrices may include but are not limited to agarose, latex, magnetic or polyacrylamide beads, silica, or polystyrene.

Following conjugation, any available sites on the matrix are blocked by appropriate reagents, and the conjugate can be used immediately or prepared for storage. The conjugates are preferably stored under conditions offering the greatest stability. Although, such conditions vary for different conjugates, optimum stability is usually achieved by dehydration, and preferably cooling to about −20° C. or less. Conjugates can also be stored hydrated in physiological buffers, at about 4° C., with the addition of an antimicrobial preservative. Suitable buffers include but are not limited to PBS, TBS, BBS, or non-saline buffers which prove effective. Typically, merthiolate (thimerosol) or sodium azide is added at 0.01 to 0.05% to retard microbial growth. Azides should not be used when conjugates are stored in metal containers.

The conjugate is then loaded into a vessel to be used for incubation with a source of IgM antibodies. Chromatography columns are the preferred incubation vessel. These can be constructed from glass, plastics, or metals, depending on the desired volume and pressure constraints. A wide range of chromatography columns are commercially available for this purpose. The volume of conjugate loaded into the vessel varies according to the dimensions of the vessel, and the quantity of IgM expected to be purified. Optimally, this volume corresponds to the IgM binding capacity of the conjugate, which is determined experimentally for each conjugate preparation. A value of about 1-20 mg per ml of conjugate would generally be preferred.

After loading into a vessel, the conjugate may be equilibrated with a buffer compatible with Osp-IgM interaction. Suitable buffers include those described above for conjugate storage, except that no preservative would be added. Once equilibrated, a sample containing IgM antibodies is added to the vessel. Optimally, a volume of sample sufficient to completely wet the conjugate is added. This usually represents about 0.3-0.5 volumes of conjugate. Typically the sample containing IgM antibodies is mammalian serum. If not, the sample should be a solution in the buffer used to equilibrate the column. The column and the sample are incubated at room temperature for about 15-60 minutes, then washed thoroughly with equilibration buffer. Buffer passing through the column is monitored for macromolecule content until such content is negligible. This is usually accomplished by measuring the absorbance (280 nm) of the buffer until it returns to the baseline value of the buffer. After washing, IgM antibodies retained within the matrix are eluted by the addition of an agent which dissociates the IgM-Osp protein complex. Examples of two of these agents are sodium dodecylsulfate (SDS) ranging in concentration from 0.1-2%, and CCS buffer comprised of 0.02M sodium cacodylate, 0.010M calcium carbonate, and 0.2M sucrose, pH 7.2, containing 0.1-1 unit of neuraminidase. Up to 90% or greater of the IgM is dissociated with SDS. Further dissociation of minute quantities of IgM has been observed with the latter treatment. The latter treatment should be avoided when removal of sialic acid residues from IgM molecule would be undesirable. Additional reagents suitable for the elution of IgM antibodies may also be employed. These include but are not limited to agents which alter the Ph, salt concentration, or hydrophobic interactions affecting the Osp-IgM interaction. Once eluted, the IgM antibodies are dialysed thoroughly against a volatile aqueous solvent, which may include solutions of 0.010 to 0.2M ammonium bicarbonate, or ammonium acetate, or distilled water, and then dried in a vacuum evaporator. The dried antibodies is preferably desiccated and stored at about 4° C. Freezing of the IgM antibodies should be avoided. Alternatively, the IgM antibodies can be dialysed into a suitable physiological buffer (see above), concentrated in a vacuum concentrator, and stored in the buffer, supplemented with an antimicrobial agent, as described above.

Other Embodiments

There are numerous additional applications for this invention beyond the epitope-independent detection and purification of IgM antibodies. The Osp-IgM interaction could be used to visualize epitope-dependent binding of IgM antibodies to specific antigens, or to recover (purify) specific antigen-antibody complexes involving IgM antibodies. Most, if not all, of the conjugates described above could be adapted for such purposes. Potential applications include, but are not limited to, determining the antigenic specificity of monoclonal or polyclonal IgM antibodies generated by mammals in response to infections or antigenic challenge, detecting, identifying and/or localizing specific antigens in biological or medical specimens, affinity-purifying specific antigens, diagnosing diseases which elicit primary and/or secondary IgM antibody-mediated immunity, and delivering neutralizing, blocking, or stimulatory antibodies and conjugates, or immunotoxins to cells or tissues which express particular antigens, including antigens characteristic of cancer or HIV infection. Some typical examples follow.

Toxoplasmosis is a disease caused by acute to chronic infection by the parasitic protozoan, *Toxoplasma gondii*. This disease is rare in healthy humans, but can cause severe pathologies in immune compromised humans, and in newborns infected congenitally. Infection by *T. gondi* typically induces a primary and prolonged IgM antibody response. These IgM antibodies could be detected in serum samples from infected individuals by protocols described above which utilize Osp protein conjugates to detect IgM antibodies. This would typically involve diluting serum samples in a physiological buffer (see above) and incubating the diluted serum for 15 to 60 minutes with antigen preparations derived from *T. gondii*. The antigens would most commonly be adsorbed to the surface of microtiter wells or immunoblot membranes. After incubation and repeated buffer washings (see above), an appropriate Osp protein conjugate would be added, and a visualization assay performed. In clinical settings the visualization would typically comprise the use of enzyme-linked Osp proteins and an ELISA reaction. Other protocols may involve autoradiography or determinations of disintegration rate of radioactive conjugates, or chemiluminescence, fluorescence, or other assays as appropriate.

Osp proteins conjugates may similarly be used to diagnose disorders associated with hypergammaglobulinemia, and hypergammaglobulinurea, and circulating immune complexes involving IgM antibodies. Such conjugates may also be used to deplete IgM antibodies from materials when desired.

Preferred Components and Conditions

If using native Osp proteins, actively growing cultures of *Borrelia burgdorferi* are needed. It is currently unknown if all isolates of *Borrelia burgdorferi* produce Osp proteins capable of binding to IgM antibodies. Two widely distributed North American isolates Sh-2-82, and B31 produce Osp proteins with such activity. Cultures are successfully maintained in BSK II medium (Barbour, A. G., 1984, "Isolation and cultivation of Lyme disease spirochetes," *Yale J. Biol., Med.,* 57:71–75), and purification techniques for the Osp proteins have been published (Dunn et al, supra, 1990, 1:159–168; France et a), 1992, "Structural analysis of an outer surface protein . . . ," *Biochem. Biophys. Acta.* [in press]). It appears from our recent results that yields of suitable Osp proteins from cultures would be increased by culturing the organisms in a medium lacking rabbit serum. Since extracellular Osp proteins bind to IgM molecules in the serum supplement, growth in serum free medium would allow recovery of uncomplexed extracellular Osp proteins. Alternatively, actively growing cultures of recombinant bacteria expressing the Osp gene products are needed. These have recently been described and are available. The recombinant Osp proteins are then purified from the recombinant hosts as previously described (Dunn et al, supra, 1990, 1:159–168; France et al, supra, 1992, *Biochem. Biophys. Acta.*).

Substances suitable for covalent or non-covalent coupling to Osp protein molecules include, but are not limited to, enzymes such as horseradish peroxidase, alkaline phosphatase, acid phosphatase, and luciferase; radioisotopes such as 125[I], 35[S], 14[C], and 3[H]; insoluble beads such as latex, agarose, polyacrylamide, and magnetic particles; solid matrices such as silica, and polystyrene; and colloidal metals such as gold. Conjugation protocols are conventionally standardized for each type of conjugate.

A variety of suitable vessels for incubation mixtures containing antibodies and antibody-binding proteins are available commercially. These include, but are not limited to multiple sample vessels such as microtiter plates and other tissue culture plasticware; vessels for western blot analysis such as staining dishes, slot dishes, and plastic bags; materials for immunofluorescence such as microscope slides, cover slips, and sterile plasticware; chromatography materials such as disposable chromatography columns, syringes, high performance and fast performance chromatography columns; vessels for incubating reagents in suspension such as test tubes, micro centrifuge tubes, beakers, and flasks; and materials for electron microscopic sample incubation such as Parlodion or Formvar-coated electron microscope grids, and Parafilm.

Components preferred for the binding reaction between Osp proteins and IgM would include the components described above; a physiological buffer compatible with the binding reaction such as PBS, TBS or others listed above, or any other buffer which might show applicability through further experimentation; a system for environmental temperature control capable of maintaining the samples at temperatures ranging from 0°–37° C.

Components preferred for the detection and/or visualization of Osp-IgM complexes may include but are not limited to the following: reagents for chromogenic detection of enzyme conjugates such as enzyme substrates, chromogenic dyes, and appropriate reaction buffers, a mechanized colorimeter compatible with the reaction vessel is advantageous for assays on numerous samples; materials for detection of radiolabeled complexes such as gamma or scintillation counters, X-ray film, and autoradiography cassettes and fluors; components for fluorescent and illuminescent detection such as fluorescent microscopes and ultraviolet light sources, fluorescence activated cell sorter, and film; and materials for IEM such as buffers, metallic stains, and an electron microscope with photographic capabilities.

Components preferred for the retention of IgM molecules onto an insoluble matrix may include, but are not limited to insoluble conjugates of Osp proteins as listed above.

Components for the recovery of IgM molecules eluted from a Osp-IgM complex may include but are not limited to: materials for chromatographic purification systems such as appropriate elution buffers, an ultraviolet absorbance detector, a fraction collector, and containers or tubes for the collection of eluted material; components for the recovery of IgM from suspended incubation mixtures would include a dissociation buffer, centrifuge, and container for collecting centrifugal supernatants.

Components preferred for the transfer, dehydration, or concentration of purified IgM antibodies may require but are not limited to the following: a dialysis system including dialysis membrane, a volatile buffer or solvent desired for maintenance of the antibodies such as those listed above, and a vessel in which to dialyse the eluate; a vacuum concentrator or vacuum evaporator to remove undesired quantities of solvent, containers to be appropriate for storing resulting volumes of antibody preparations, and antimicrobial preservative for maintenance of antibody solutions (see above).

The functional characteristics preferred for native Borrelia burgdorferi cultures grown in BSK II or serum free medium would be growth to a density of $3 \times 10^7$ to $1 \times 10^5$ organisms per ml. Recombinant organisms expressing the Osp proteins would be expected to produce about 1–20 mg of Osp protein per liter of liquid culture.

The characteristics required for incubation vessels vary in relation to the particular applications. Thorough protocols for such applications specify vessels appropriate for particular applications, and are readily available.

Advantages Over Conventional Techniques

In addition to advantages described above, the prokaryotic IgM-binding system of the present invention offers several additional advantages over conventional systems currently available. One major advantage associated with the use of bacterial proteins is advantageously low cost and improved chemical stability. Recent work has shown that the Osp proteins are advantageously very stable during storage and biochemical manipulation. Bacterial cultures, such as those useful for obtaining the binding substances employed in the present invention, are also relatively inexpensive to start and maintain.

On the other hand, most conventional systems rely on secondary anti-IgM antibodies to form complexes with targeted IgM molecules. Production of such secondary antibodies requires propagation either in mammals or in mammalian cell culture facilities, both of which involve considerably greater expense and procedural controls than bacterial cultures. Furthermore, complexes between interactive antibody molecules require denaturation for dissociation, with variable losses of activity upon renaturation Two non-antibody-based systems for IgM purification have also been marketed, but these systems suffer from several disadvantages. The first utilizes streptococcal protein G to deplete serum of IgG antibodies, which leaves samples relatively enriched with IgM. However, this technique does not remove other serum proteins which include antibodies of the IgA, IgD, and IgE classes, serum albumin, complement, and others. A second method uses a lectin (carbohydrate binding protein) to bind, apparently preferentially, to the oligosaccharide moiety of IgM. The manufacturers of this product indicate that other serum glycoproteins, such as the other classes of antibodies, are not bound by this lectin. Lectins, being eukaryotic products, are relatively expensive to acquire. They are extracted from plant and animal tissue, rather than bacterial cultures. Furthermore, they can be unstable over time. The present invention overcomes these problems associated with conventional techniques.

Analysis of Interactions between Outer Surface Proteins and IgM Antibodies

By analyzing the components of a predominant extracellular vesicle-associated 83 kDa protein band, it was found that certain extracellular B. burgdorferi proteins interact with the $\mu$ chain of IgM. The interaction produces a multi-protein complex that is abundant in B. burgdorferi cultures, and resembles structurally-similar material that has previously been detected in fluids and tissues from infected hosts. Furthermore, the results suggest that the complex can occur within in vitro cultures, incorporating non-B. burgdorferi-directed IgM antibodies.

The n-terminal peptide sequence of the major component of the band corresponded to mammalian Ig $\mu$ chain. Therefore, it was concluded that this extracellular band is distinct from the 83 kDa cellular protein described by LeFebvre and others (LeFebvre, R. B., G-C. Perng, and R. C. Johnson, 1990. The 83-kilodalton antigen of Borrelia burgdorferi which stimulates immunoglobulin M (IgM) and IgG responses in infected hosts is expressed by a chromosomal gene. J. Clin. Microbiol. 28:1673–1675). Failure to co-detect the Osp or other sequences could result from either a low relative quantity of such proteins in the band, or n-terminal acylation of the mature Osp proteins, or both. Similarly, since the amino acid composition of this band reflected IgM, it was presumed that the relative molar ratios of other proteins in the band is low.

Clearly, the 83 kDa band in extracellular concentrates contains a mixture of proteins. Two lines of evidence indicate that quantities of OspA and OspB are retained within an electrophoretic protein band at 83 kDa. In a previous study (Dorward et al., 1991, pp. 1162–1171), and in subsequent experiments (Dorward, D. W. and C. F. Garon. Unpublished results.), rabbits immunized with proteins contained within this band consistently developed a pronounced IgG antibody response to the Osp proteins. The present inventors found that OspA and OspB could also be detected in gels and on immunoblots after excision, neuraminidase treatment, and re-extraction of the 83 kDa band. Inconsistent binding by anti-Osp monoclonal and polyclonal antibodies to the 83 kDa band, and minimal intrinsic labeling of proteins migrating at 83 kDa suggest that relatively little *B. burgdorferi* protein is present in the band.

The presence of IgM in extracellular concentrates was confirmed by antibody recognition and reduction sensitivity. Electrophoretic retardation of the unreduced protein greatly exceeded the predicted value of 150-180 kDa for monomeric Ig molecules. Furthermore, the reduction-sensitive bands reacted with $\mu$-chain specific antisera, but not with $\gamma$-chain specific reagents including protein A, protein G, and anti-rabbit IgG antibodies (data not shown). Immune electron microscopy and immune precipitations demonstrated that the apparent interaction between IgM and the Osp proteins occurs extracellularly. When cultured spirochetes and extracellular concentrates were probed with antibodies specific for either OspA or OspB, and $\mu$-chain, and the antibodies were labeled with different sized gold spheres, the majority of both size classes of spheres was concentrated on extracellular amorphous material. These results were consistent with previous immune electron microscopic findings of amorphous aggregates of extracellular antigens, including OspA and OspB, in fluids and tissues of infected hosts (Dorward et al., 1991, 1162-1171). Relatively little of the labeled material was retained directly on cell or membrane surfaces, suggesting that surface-exposed epitopes, recognized by monoclonal antibodies 5332 and 5TS (Barbour, A. G., S. L. Tessier, and W. J. Todd, 1983. Lyme disease spirochetes and ixodid tick spirochetes share a common surface antigenic determinant defined by a monoclonal antibody *Infect. Immun.* 41, 795-804; Barbour et al., 1984, 94-100), are located primarily on exported forms of OspA and OspB. This observation was supported by immune precipitation results using the anti-$\mu$ chain antibody-colloidal gold conjugates. Precipitation of filter-sterilized culture supernatants with this conjugate resulted in the specific and simultaneous recovery of IgM, OspA, and OspB.

The experimental results suggest that at least two interactions between IgM and the Osp proteins may occur. The results of immune precipitations demonstrated that significant quantities of Osp-IgM complexes are dissociated by extraction with SDS and 2-mercaptoethanol. Although further dissociation of Osp proteins and IgM antibodies present in the 83 kDa band did not occur after chelation with 50 mM EDTA, and salt treatments including 1M NaCl and 4M $MgCl_2$ failed (data not shown), an additional fraction of the Osp proteins was released from the 83 kDa band by neuraminidase treatment and re-extraction with "Laemmli buffer." This suggests that the Osp proteins, or other associated *B. burgdorferi* proteins, can interact with reduced $\mu$ chains, and that sialic acid residues may contribute to the retention of Osp proteins within the 83 kDa band in gels. Whether this enzymatic disruption of the protein complex indicates a covalent or other stable interaction between the constituents remains to be determined. Neuraminidase treatment also caused a marked decrease in the apparent mass of the majority of $\mu$ chain molecules migrating at 83 kDa. Since $\mu$ chain molecules can exhibit apparent molecular masses of between 57 and 84 kDa depending on degree of glycosylation and whether the IgM is secreted or incorporated on the surface of B lymphocytes, and since the effect of *B. burgdorferi* peptides on the migration of $\mu$ chains is unclear, such a shift in migration could result from the dissociation of Osp proteins, deglycosylation, or both. Furthermore, although proteinase inhibitors were included during neuraminidase treatments, we can not rule out the possibility that proteolysis also contributed to the dissociation of Osp proteins and $\mu$ chains. Whether the *B. burgdorferi* proteins bind directly to sialic acid or whether the neuraminidase treatment interrupts the interaction by a steric or conformational change in the IgM or spirochetal proteins remains unclear. The involvement of glycosylated $\mu$ chains in interactions between IgM and these extracellular proteins may, however, contribute to explanations for the affinity of certain lectins for extracellular *B. burgdorferi* antigens the 83 kDa band, and other specific *B. burgdorferi* proteins, Lyme disease and related disorders.

MATERIALS AND METHODS

Bacteria. *Borrelia burgdorferi* strain Sh-2-82, was maintained at 36° C., in BSK II medium, as previously described (Barbour, A. G. 1984. Isolation and cultivation of Lyme disease spirochetes. *Yale J. Biol. Med.* 57:71-75). The medium was prepared freshly, and was not heat-inactivated. Serum-free cultures of this strain were also provided by Dr. Andrew Szczepanski.

Recovery of whole cells and extracellular materials. Whole cells (WC), extracellular vesicles, and vesicle-associated materials were recovered from cultures by differential and sucrose density-gradient centrifugation according to previously published procedures (Dorward, D. W., and C. F. Garon. 1989. DNA-binding proteins in cells and membrane blebs of *Neisseria gonorrhoeae*. *J. Bacteriol.* 171:4196-4201; Garon, C. F., D. W. Dorward, and M. D. Corwin. 1989. Structural features of *Borrelia burgdorferi*-the Lyme disease spirochete: silver staining for nucleic acids. *Scanning Microscopy*, 3:109-115). Culture supernatants were filter-sterilized using nitrocellulose membranes with 0.22 $\mu$m porosity (Nalge Co., Rochester, N.Y.), prior to recovery of extracellular products. Pellets containing extracellular products were either resuspended in appropriate buffers for electron microscopy, enzymatic treatment, or electrophoresis (see below), or stored at −20° C.

Electrophoresis. Whole cells and extracellular products were solubilized and subjected to SDS-PAGE, using the discontinuous buffer system of Laemmli (Laemmli, U. K. 1970. Cleavage of structural proteins during the assembly of the head of bacteriophage T4. *Nature* (London) 227:680-68517), with published modifications (Judd, R. C. 1982. $^{125}$I-peptide mapping of protein III isolated from four strains of *Neisseria gonorrhoeae*. *Infect. Immun.* 37:622-631). The separated proteins were either stained with Coomassie brilliant blue (CBB) and destained with deionized water, or were electroblotted onto nitrocellulose membranes as previously described (Batteiger, R., W. J. Newhall, and R. B. Jones. 1982. The use of Tween 20 as a blocking agent in the immunological detection of proteins transferred to nitrocellulose membranes. *J. Immunol. Methods.* 55:297-307), or onto polyvinylidene difluoride (PVDF) membranes (Millipore, Corp., Bedford, Mass.), according to the manufacturer's recommendations. For experiments assessing the effects of reduction on protein migration, extracellular concentrates or gel segments containing specific proteins were also extracted in "Laemmli buffer" lacking 2-mercaptoethanol.

Amino acid analysis. Electrophoretically separated *B. burgdorferi* vesicle-associated proteins were electroblotted onto PVDF membranes as described above, and stained with CBB. Excised segments of PVDF membranes, containing the 83 kDa band were hydrolyzed for 2 hr, at 160° C., in the vapor phase of 6N HCl and 2% (v/v) liquified phenol. Membrane segments were then rinsed with 40% acetonitrile, followed by 0.5% trifluoroacetic acid in 40% acetonitrile to recover the hydrolyzed amino acids. Phenylthiocarbamoyl-amino acid analysis was performed on a model 420A derivitizer coupled to a model 130A separation system (Applied Biosystems, Inc., Foster City, Calif.). The determined amino acid composition was compared to compositions of all 35-90 kDa proteins contained in the Martinsrieder Institut für Proteinsequenzen, MIPSX version 17.0 protein database (Martinsried, FRG.), using program A3COMP (9) to identify similar compositions.

Protein sequencing. Excised segments of PVDF membranes containing the 83 kDa band were also used for protein sequencing. Sequencing was enabled by removal of a pyroglutamate residue from the N-terminus. A PVDF segment containing 19 $\mu$g of protein was pre-treated with 0.5% polyvinylpyrrolidone-40 (Sigma Chemical Co., St. Louis, Mo.) in 100 mM acetic acid, for 30 min at 37° C. Following 10 water washes, the segments were incubated under nitrogen for 5 hr, at 4° C., with 5 $\mu$g of calf liver pyroglutamate aminopeptidase (Boehringer Mannheim Biochemicals, Indianapolis, Ind.) in buffer containing 100 mM dibasic sodium phosphate, 10 mM disodium EDTA, 5 mM dithiothreotol, and 5% (v/v) glycerol, pH 8.0. Incubation was continued for 16 hr at 30° C., after adding an additional 5 $\mu$g of enzyme, and the treated segment was rinsed twice with water. Sequencing was performed in the gas phase, on a model 477A protein sequencer, with on-line model 120A analyzer (Applied Biosystems, Inc.), and model 2600 chromatography software (Nelson Analytical, Cuertino, Calif.).

Antibodies and immunoblot analysis. Supernatants from hybridomas 5332 and 5TS, which recognize OspA and OspB, respectively (Barbour, A. G., S. L. Tessier, and W. J. Todd. 1983. Lyme disease spirochetes and ixodid tick spirochetes share a common surface antigenic determinant defined by a monoclonal antibody. *Infect. Immun.* 41:795-804; Barbour et al., 1983, pp. 795-804), were graciously provided by Tom Schwan (Rocky Mountain Laboratories, Hamilton, Mont.). Purified murine monoclonal IgM was a gift of William Knowles (Miles Laboratories, West Haven, Conn.) Goat anti-rabbit $\mu$ chain antiserum and horseradish peroxidase (HRP)-conjugated goat anti-rabbit $\mu$ chain antibodies were purchased from Organon Technika-Cappel (Durham, N.C.). Goat anti-mouse $\mu$ chain antibodies, protein G, and protein A-HRP were purchased from Sigma Chemical Co. Colloidal gold conjugates of protein G and anti-$\mu$ chain antibodies were produced for this study, according to previously published procedures (Robinson, E. N., Z. A. McGee, J. Kaplan, M. E. Hammond, J. K. Larson, T. M. Buchanan, and G. K. Schoolnik. 1984. Ultrastructural localization of specific gonococcal macromolecules with antibody-gold sphere immunological probes. *Infect. Immun.* 46:361-366). These antibodies were used to probe electroblotted WC and extracellular antigens, and resulting immune complexes were detected by peroxidase staining, as previously described (Batteiger et al., 1982, pp. 297-307), using appropriate immune-peroxidase conjugates.

Immune electron microscopy. Parlodion-coated electron microscopy grids were "activated" with anti-vesicle F(ab')$_2$ fragments as previously described (Dorward et al., 1991, pp. 1162-1171). Whole cells, extracellular concentrates, or uninoculated media were incubated with the grids for 20 min at room temperature, then washed, probed with antibodies, and labeled with appropriate colloidal gold conjugates, as previously described (Dorward et al., 1991, pp. 1162-1171; Robinson, E. N., Z. A. McGee, J. Kaplan, M. E. Hammond, J. K. Larson, T. M. Buchanan, and G. K. Schoolnik. 1984. Ultrastructural localization of specific gonococcal macromolecules with antibody-gold sphere immunological probes. *Infect. Immun.* 46:361-366). After labeling, the grids were washed briefly with 0.25M ammonium acetate, negatively-stained with 0.5% ammonium molybdate, pH 6.5, and observed at 75 kV with an transmission electron microscope (Hitachi, Ltd., Tokyo, Japan).

Immune precipitation. Components of filter sterilized culture supernatants were immune precipitated from solution using 30 nm colloidal gold conjugates of either anti-rabbit or anti-mouse $\mu$ chain antibodies. Five ml of supernatant from standard BSK II cultures, or from serum-free cultures containing or lacking murine monoclonal IgM antibodies, were incubated at 25° C. for 1 hr, with 1 ml of conjugate containing approximately 30 $\mu$g of anti-$\mu$ chain antibodies. Resulting immune complexes were recovered by centrifugation at 38,500× g in a TLA 45 rotor (Beckman Instruments, Palo Alto, Calif.). Pellets were washed twice by resuspending in sterile dPBS, and recovering by centrifugation. Samples of uninoculated media, incubated with the conjugate, and samples of filtered supernatant, incubated with stabilizing buffer lacking the conjugate, were also prepared as described. Washed pellets were then extracted in Laemmli buffer for subsequent electrophoretic and immunoblot analyses.

Neuraminidase treatment. For neuraminidase treatment of the 83 kDa band, SDS-PAGE gels were stained with CBB in water, and the 83 kDa band was excised. Excised gel segments were macerated in 20 $\mu$l of buffer containing 20 mM sodium cacodylate, pH 7.2, 10 mM CaCl$_2$, 200 mM sucrose, and 1 $\mu$g each of proteinase inhibitors aprotinin, bestatin, and E-64 (Boehringer Mannheim Biochemicals), which also contained or lacked 0.1 unit of neuraminidase (United States Biochemical Corp., Cleveland, Ohio). After incubation for 16 hr, at 4° C., the mixtures were extracted with 20 $\mu$l of Laemmli buffer, containing 4% SDS, and the liquid phase was retained for subsequent electrophoresis. The second gels were electroblotted onto nitrocellulose, probed with either a mixture of monoclonal antibodies 5332 and 5TS, followed by Protein A-HRP, or anti-rabbit $\mu$ chain-HRP. Antibody binding was visualized by peroxidase staining.

Accession number. The n-terminal amino acid sequence determined for the 83 kDa peptide was entered in the National Biomedical Research sequence library. The accession number is A37272.

RESULTS

Previous work with *B. burgdorferi* extracellular vesicle preparations demonstrated a highly concentrated protein band, with an electrophoretic migration of 83 kDa, and an uncharacterized relationship with OspA and OspB. In order to identify the predominant peptide present in the band, the electroblotted vesicle-associated proteins were electroblotted onto PVDF membranes, the 83 kDa band excised, and the amino acid composition determined with the results shown in Table 1.

TABLE 1

| Amino acid composition of the 83 kDa band | | | |
|---|---|---|---|
| Amino acid | Mole % | Amino acid | Mole % |
| Ala | 6.25 | Lys | 4.26 |
| Arg | 2.94 | Met | 0.59 |
| Asx | 9.46 | Phe | 4.37 |
| Glx | 10.75 | Pro | 6.94 |
| Gly | 7.43 | Ser | 14.80 |
| His | 1.22 | Thr | 8.39 |
| Ile | 2.71 | Tyr | 2.72 |
| Leu | 7.83 | Val | 9.35 |

Cys and Trp not determined.

Figure 1:
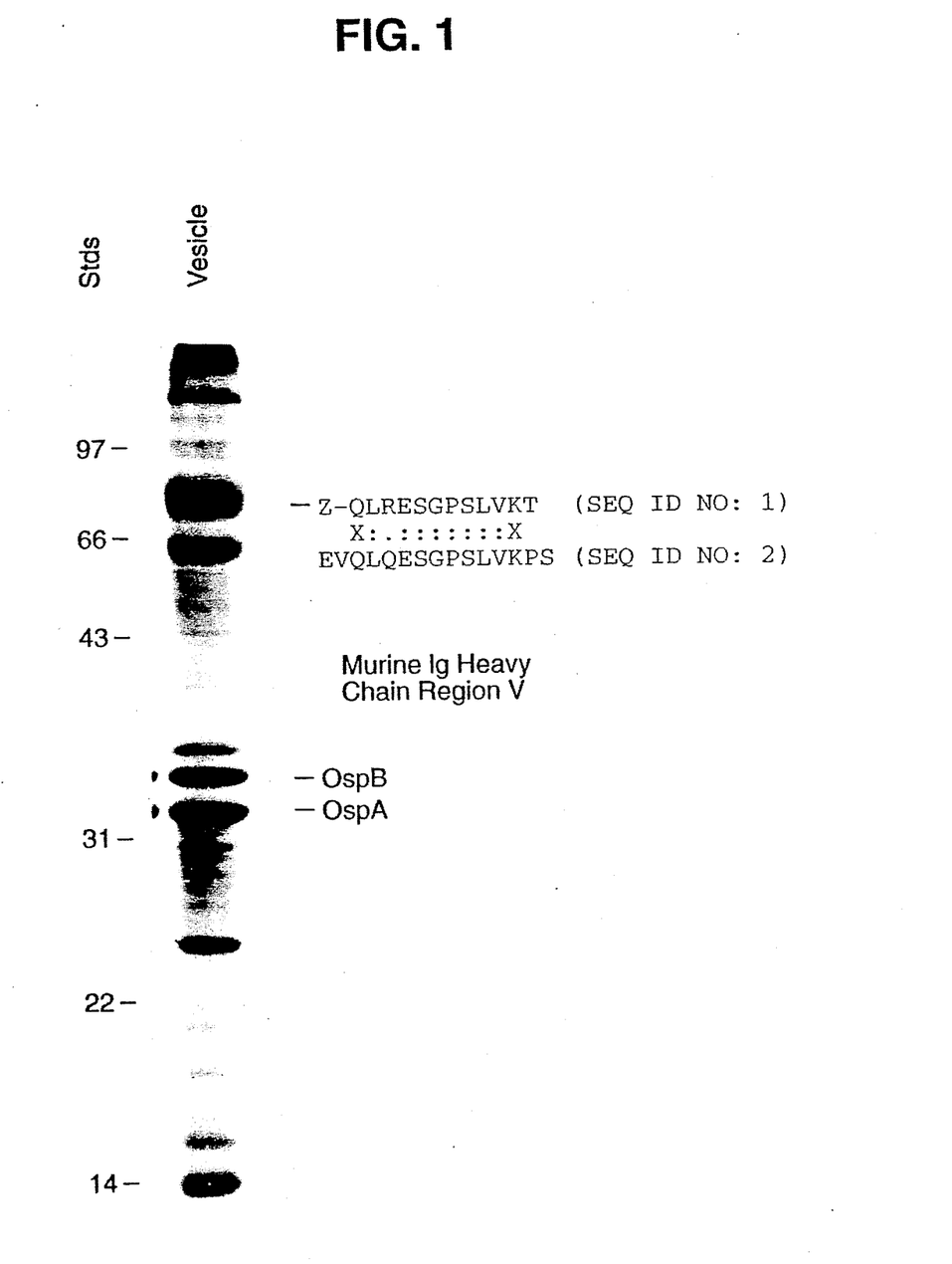
FIG. 1 shows the electrophoretic position and N-terminal sequence of a major component of the 83 kDa major extracellular protein band.

The N-terminal amino acid sequence shown in FIG. 1 was also determined. Extracellular concentrates were separated by SDS-polyacrylamide gel electrophoresis, electroblotted onto PVDF membranes, and stained with Coomassie blue. The 83 kDa band was excised and sequenced. Residues 3–14 (upper sequence) were then screened for sequence homology with the National Biomedical Research Foundation database. The partial sequence (NBRF A37272, SEQ ID. NO.) shared 91.9% identity with the N-terminus of Ig heavy chain from a mouse (lower sequence) (NBRF A02098). The region of identity is delineated between two "Xs." (Stds, molecular mass standards in kilodaltons.) FIG. 1 shows the 83 kDa band within a CBB-stained 12.5% SDS polyacrylamide gel, and the sequence obtained for residues 1–14 (upper sequence, FIG. 1). Residue 1 was pyroglutamate, residue 2 could not be identified, and residue 10 was tentatively identified as serine. An example of the results of a sequence homology search is also shown (lower sequence, FIG. 1). This partial sequence was compared with the National Biomedical Research Foundation protein sequence bank using the FASTA program (Pearson, W. R., and D. J. Lipman. 1988. Improved tools for biological sequence comparison. *Proc. Nat. Acad. Sci.* (U.S.A.). 85:2444–2448), and it was found that up to 11 of 12 aligned residues were identical with N-terminal residues of Ig heavy chain from a variety of mammals. Furthermore, a comparison of the amino acid composition with proteins in the Martinsrieder Institut für Proteinsequenzen database showed the greatest identity with IgM.

Figure 2:
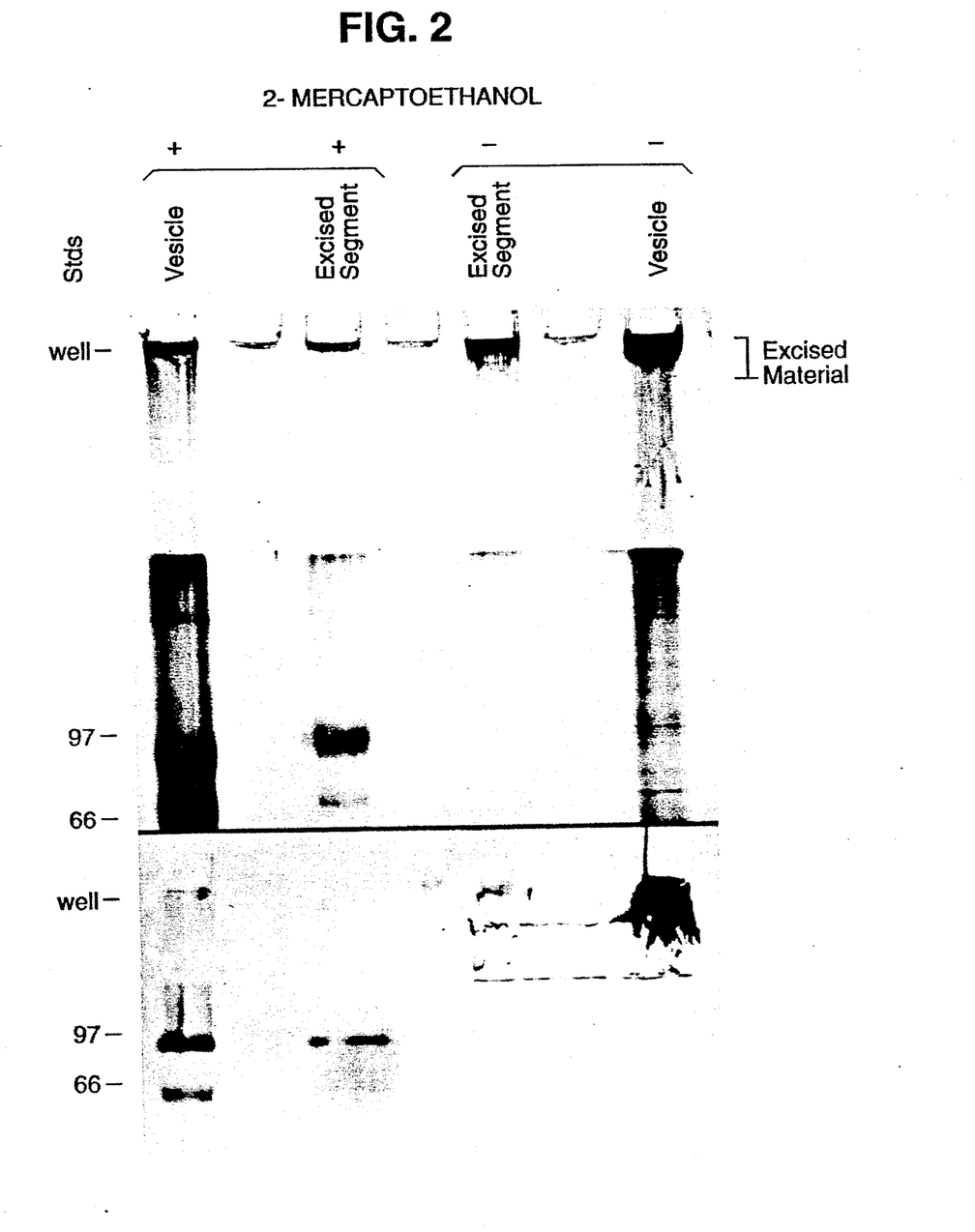
FIG. 2 is a photograph showing the effect of reduction on the electrophoretic migration of the 83 kDa vesicle-associated protein band.

In order to determine whether the sequenced peptide was derived from intact monomeric or oligomeric antibody molecules, the effects of reduction on the migration of the 83 kDa band was examined. FIG. 2 shows the pertinent portions of a CBB-stained gel (FIG. 2a), and an immunoblot (FIG. 2b). Extracellular concentrates were extracted in "Laemmli" buffer containing or lacking 2-mercaptoethanol, then separated by SDS-PAGE. In preparations lacking 2-mercaptoethanol, the 83 kDa band was not detected, but an accumulation of protein was evident in the "stacking" gel, just under the loading well (2a). When this accumulated protein was excised, re-extracted with or without 2-mercaptoethanol, the unreduced extract remained in the stacking gel, whereas the reduced extract migrated at 83 kDa. When an immunoblot of the same preparations was probed with anti-rabbit $\mu$ chain antibody-peroxidase conjugates and visualized by peroxidase staining, both the 83 kDa band and the accumulated protein in the stacking gel were stained (2b). (Stds, molecular mass standards in kilodaltons.) When extracted with Laemmli buffer lacking 2-mercaptoethanol, extracellular preparations lacked the concentrated staining at 83 kDa, and protein accumulated in the "stacking gel," just below the loading well (FIG. 2a). When the gel segment containing the accumulated protein was excised, and re-extracted the segment with Laemmil buffer containing 2-mercaptoethanol, the 83 kDa band was restored. Without reduction the re-extracted protein again accumulated in the stacking gel. An electroblot containing these preparations with anti-$\mu$ chain-HRP was also probed, then the antibody binding visualized by peroxidase staining (FIG. 2b). Both the 83 kDa band and the unreduced protein which accumulated in the stacking gel reacted strongly with this antibody. An additional labeled band at 57 kDa, which is characteristic of Ig heavy chain, was detected in the reduced extracellular protein preparation. Light chain molecules were also detected at approximately 30 kDa in reduced preparations using heavy and light chain-specific reagents (data not shown).

Figure 3A:
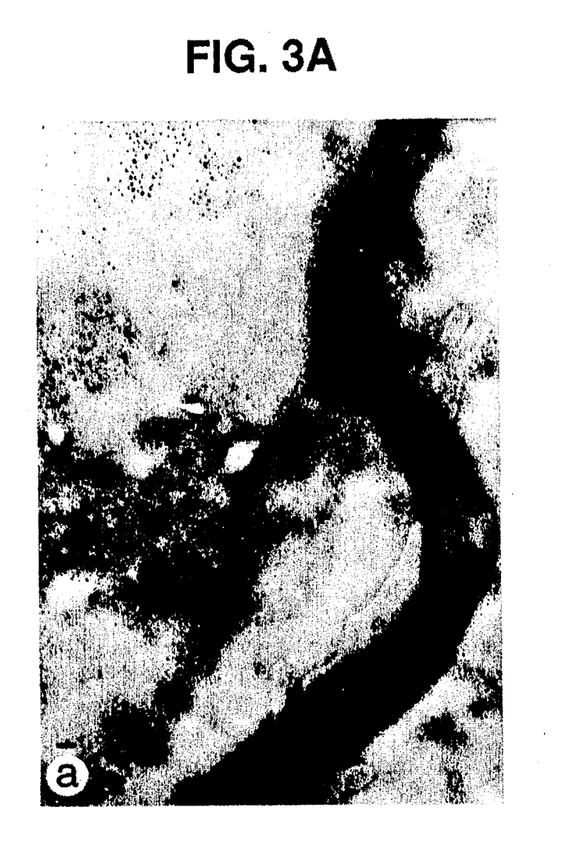
FIGS. 3a–3e are a photograph showing the extracellular association of epitopes for IgM, OspA and OspB, in cultures of *B. burgdorferi*.
Figure 3B:
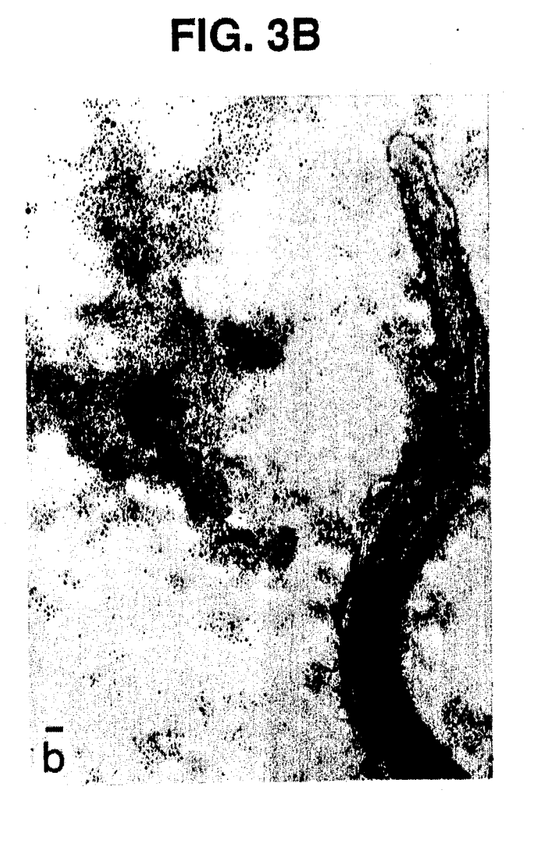
Figure 3C:
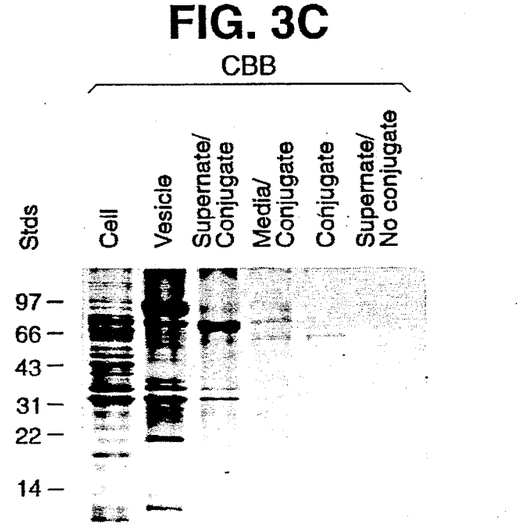
Figure 3D:
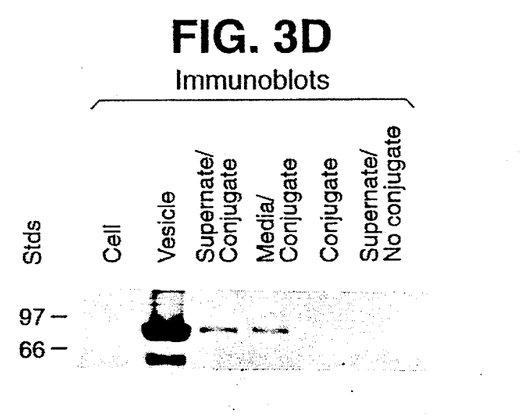
Figure 3E:
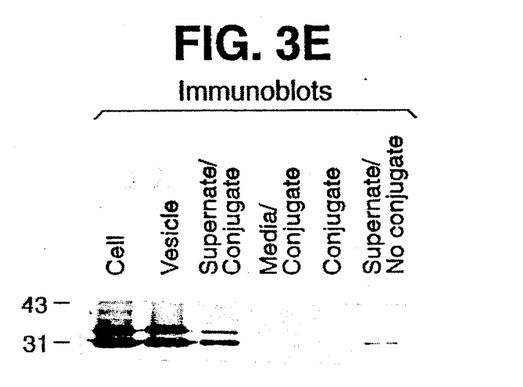

Since previous work had demonstrated that rabbits immunized with the 83 kDa band produced antibodies that reacted with OspA and OspB, immune electron microscopy and immune precipitation were used to determine whether these proteins interact within in vitro cultures. FIG. 3 is a composite of micrographs and segments of an SDS-PAGE gel and immunoblots that show the results of the experiments. FIGS. 3a and 3b are immune electron micrographs of mid-log phase *B. burgdorferi* cultures that were probed with IgG monoclonal antibodies to OspA (FIG. 3a) or OspB (FIG. 3b), and labeled with both anti-rabbit $\mu$-chain antibodies, conjugated to 15 nm gold spheres, and 7 nm gold-protein G conjugates. Gold spheres of both size classes were concentrated on amorphous aggregates of antigen present in *B. burgdorferi* cultures. Relatively little label was observed bound directly to cell or membrane surfaces. Similar amorphous aggregates were labeled by both classes of spheres in extracellular concentrates and only sparse randomly-distributed gold was observed on grids incubated with uninoculated media (data not shown). When proteins that could be precipitated from filter-sterilized culture supernatants with anti-$\mu$ chain-colloidal gold conjugates were examined by SDS-PAGE and immunoblot analysis (FIG. 3c-e), it was found that certain proteins co-precipitated. A CBB-stained 12.5% gel (FIG. 3c) shows that an 83 kDa protein band was precipitated from culture supernatants and uninoculated media. Additional bands at 34, 32, 24, and 14 kDa were evident in precipitants from culture supernatants. Only marginal staining of the 32 kDa band was detected in preparations from culture supernatants in which the immune conjugate was replaced by buffer. Immunoblots of these preparations indicated that the precipitated 83 kDa band contained $\mu$ chain (FIG. 3d), and the 32 and 34 kDa bands that co-precipitated with the IgM were OspA and OspB (FIG. 3e).

Figure 4:
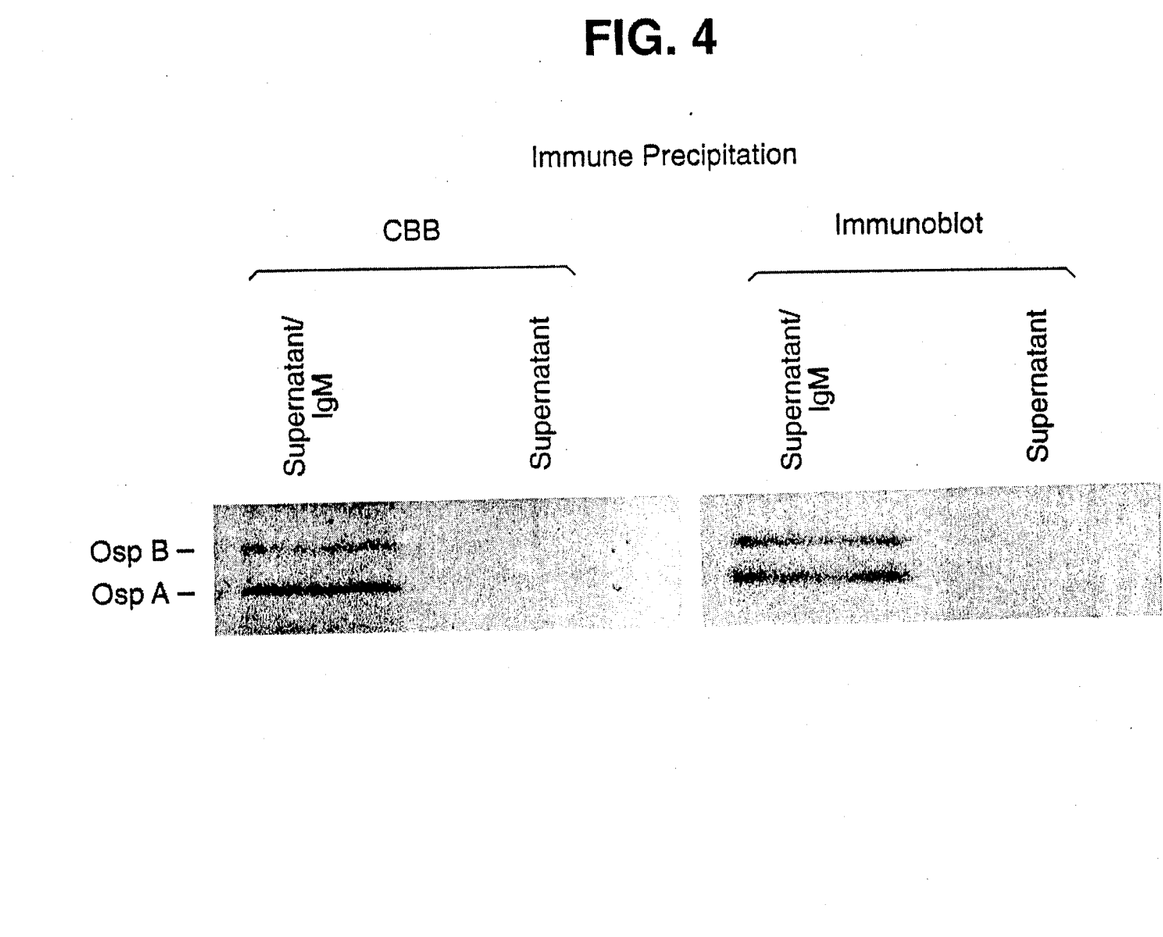
FIG. 4 is a photograph showing the co-precipitation of *B. burgdorferi* proteins and non-specific monoclonal IgM antibodies.

In order to evaluate whether the interaction between IgM and *B. burgdorferi* resulted from classic antigen-antibody binding or other mechanisms, the organisms were cultivated in media lacking rabbit serum and were examined to determine whether a similar Osp-IgM complex could form in culture upon addition of murine monoclonal IgM antibodies, specific for glycosylated human serum albumin. FIG. 4 shows co-precipitation of *B. burgdorferi* proteins and non-specific monoclonal IgM antibodies. Serum-free cultures were supplemented with murine monoclonal IgM antibodies directed against glycosylated human serum albumin, or left un-supplemented. Antigens present in filter-sterilized culture supernatants were precipitated using anti-mouse IgM antibody-colloidal gold conjugates, and subjected to SDS-PAGE and immunoblot analysis. Precipitants from cultures supplemented with IgM antibodies contained proteins at 32 and 34 kDa, which were identified as OspA and OspB by reactivity with monoclonal antibodies. These proteins were not detected in precipitants from cultures lacking IgM antibodies. Stds, molecular mass standards in kilodaltons. Equivalent cell growth was observed in cultures containing or lacking monoclonal IgM. Using colloidal gold conjugates of anti-mouse μ chain-specific antibodies to precipitate antigens from filter-sterilized supernatants of such cultures, OspA and OspB co-precipitated with IgM, but the Osp proteins were not detected in precipitants from supernatants lacking the supplemental monoclonal antibodies.

In order to identify components in the excised 83 kDa band that might induce anti-Osp rabbit antibodies, it was examined whether it was possible to dissociate detectable quantities of the Osp proteins from the 83 kDa band. Initially it was found that treatment of extracellular concentrates with agent including 50 mM EDTA, 1M NaCl, 4M MgCl$_2$, and 100 mM sodium borate at pH 10.4 failed to alter the relative concentrations of the Osp proteins and the 83 kDa band in SDS-PAGE gels. However, treatment with glycosidases including endoglycosidase F, endo-N-acetylgalactosaminidase, and neuraminidase resulted in a marked reduction in the apparent quantity of the 83 kDa band and a corresponding increase in staining at OspA and OspB (data not shown). In order to determine whether the glycosidase treatment acted directly on the 83 kDa band, the band was excised, incubated with buffer containing or lacking neuraminidase, the products with Laemmli buffer were re-extracted, and the products examined by immunoblot analysis.

Figure 5A:
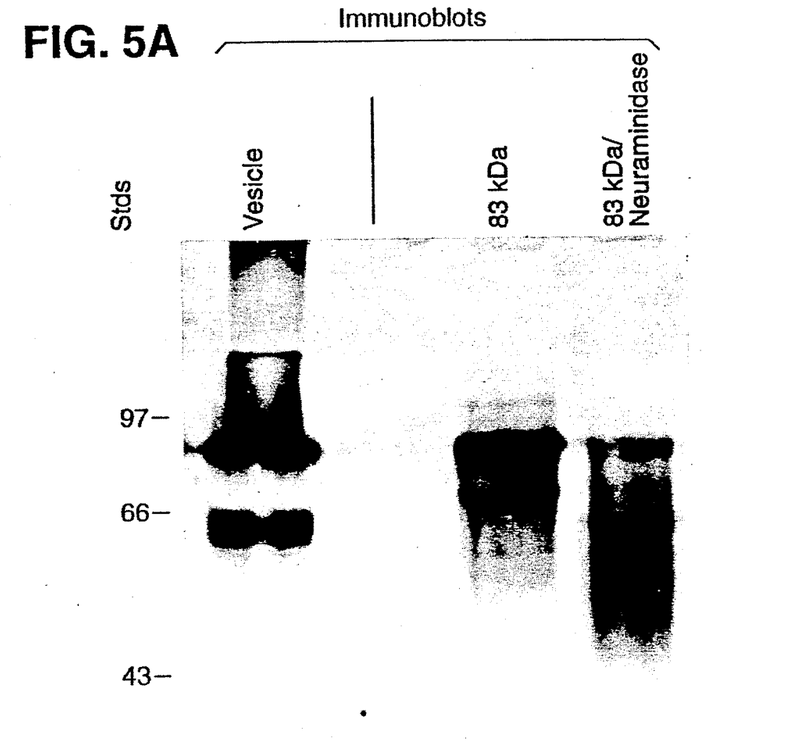
FIGS. 5a–5b show the effect of neuraminidase treatment on the 83 kDa vesicle-associated protein band.
Figure 5B:
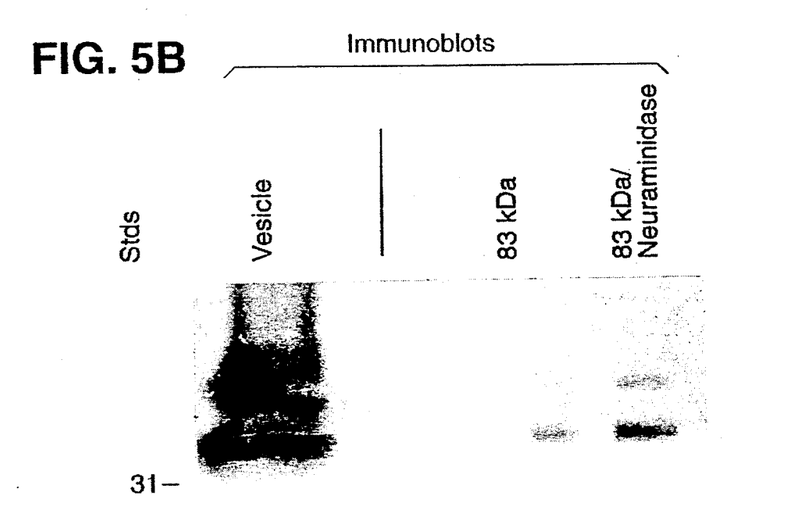

FIG. 5 shows the effect of neuraminidase treatment on the 83 kDa vesicle-associated protein band. Extracellular proteins were separated by SDS-PAGE, and the 83 kDa bands were excised from the gel. Gel segments were macerated and incubated with buffer containing neuraminidase and proteinase inhibitors, or buffer and the inhibitors only. Such mixtures were then re-extracted and examined by immunoblot analysis, using anti-μ chain antibodies (5a) and monoclonal antibodies to OspA and OspB (5b). Neuraminidase treatment resulted in both an electrophoretic shift in the μ chain from 83 to products at 57 kDa and 45–55 kDa, and increased labeling and detection of OspA and OspB proteins. (Stds, molecular mass standards in kilodaltons.) The figure shows portions of two immunoblots that were probed with either polyclonal anti-μ chain antibodies (FIG. 5a), or with monoclonal antibodies against OspA and OspB (FIG. 5b). Although OspA was detectable in the lane containing the untreated 83 kDa protein, neuraminidase treatment increased the labeling of OspA and OspB. The treatment also caused a shift in the migration of μ chain from 83 kDa, resulting in a distinct band at 57 kDa and diffuse products near 45–55 kDa. Similar results were observed when the 83 kDa band was excised from gels containing material that had been precipitated from culture supernatants with anti-μ chain-colloidal gold conjugates (data not shown).

The invention being thus described, it will be obvious that the same may be varied in many ways. Such variations are not to be regarded as a departure from the spirit and scope of the invention and all such modifications as would be obvious to one skilled in the art are intended to be included within the scope of the following claims.

---

What is claimed is:

1. A method for isolating IgM from a fluid sample comprising the steps of:
   (a) contacting said fluid sample suspected of containing IgM with a binding substance comprising an outer surface protein (Osp) Borrelia burgdorferi, Borrelia burgdorferi cells, or cellular or extracellular components obtained or derived from said cells which contain said Osp, under conditions favorable for the binding of IgM to said binding substance to form IgM-binding substance complexes, wherein said fluid sample is obtained from a test subject not previously exposed to Borrelia burgdorferi antigens; and
   (b) dissociating IgM from said complexes.

2. The method of claim 1, wherein complexes formed by binding of IgM with said binding substance are separated from the remainder of said fluid sample.

3. The method of claim 2, wherein said binding substance is immobilized to a solid substrate prior to contacting said fluid sample with said binding substance, and said solid substrate is separated from the remainder of said fluid sample.

4. The method of claim 3, wherein the separated solid substrate is exposed to a liquid effective to dissociate bound IgM.

5. The method of claim 1, wherein said binding substance is a component of B. burgdorferi cells which forms an extracellular complex with IgM upon contacting IgM with viable cells of B. burgdorferi.

6. The method of claim 1, wherein said outer surface protein is OspA or OspB.

7. A method of purifying IgM from a fluid sample obtained from a test subject not previously exposed to B. burgdorferi antigens which comprises:
   a) contacting said fluid sample with an affinity substrate comprising a solid substrate having immobilized thereon an outer surface protein (Osp) of Borrelia burgdorferi, wherein the contacting is performed under conditions favorable to binding IgM to the immobilized outer surface protein,
   b) contacting the affinity substrate obtained from step a) with a liquid which dissociates IgM from the immobilized outer surface protein, and
   c) recovering dissociated IgM.

8. The method of claim 7, wherein said outer surface protein is OspA.

9. The method of claim 7, wherein said outer surface protein is OspB.

10. A method for detecting IgM in a fluid sample suspected of containing IgM, said fluid sample obtained from a test subject not previously exposed to Borrelia burgdorferi antigens which comprises:
    a) contacting said fluid sample with a binding substance comprising an outer surface protein (Osp) of Borrelia burgdorferi, Borrelia burgdorferi cells, or cellular or extracellular components obtained or derived from said cells which contain said Osp, under conditions favorable to binding of IgM to said binding substance to form IgM-binding substance complexes, and
    b) detecting said complexes formed by means of a label conjugated to said binding substance or by means of a labeled reagent that specifically binds to said complexes subsequent to their formation.

11. The method of claim 10, wherein said outer surface protein is OspA.

12. The method of claim 10, wherein said outer surface protein is OspB.

13. The method of claim 10, wherein said binding substance is said outer surface protein (Osp) which is immobilized on a solid substrate and wherein detecting step b) comprises:
- i) contacting said complexes with a reagent conjugated with a detectable label wherein said reagent specifically binds to IgM, and
- ii) detecting said detectable label.

14. The method of claim 10, wherein said binding substance is said outer surface protein which is conjugated with a detectable label and wherein detecting step b) comprises:

- i) separating said complexes from unbound labeled outer, surface protein, and
- ii) detecting said detectable label which is present in said complexes or which is unbound.

15. The method of claim 14 further comprising:
- i) contacting said complexes with a reagent immobilized on a solid substrate to form immobilized complexes thereon wherein said reagent binds to IgM present in said complexes, and
- ii) separating said immobilized complexes from the remaining mixture.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( D ) TOPOLOGY: linear     ( i i ) MOLECULE TYPE: peptide     ( i i i ) HYPOTHETICAL: NO     ( v ) FRAGMENT TYPE: N-terminal     ( v i ) ORIGINAL SOURCE:
        ( A ) ORGANISM: Borrelia burgdorferi     ( i x ) FEATURE:
        ( A ) NAME/KEY: Peptide
        ( B ) LOCATION: 1..14
        ( D ) OTHER INFORMATION: /label=peptide
            / note="amino terminal sequence of 82 kDa peptide.
            Residue 1 is pyroglutamic acid, residue 2 is
            unidentified, Residues 3-13 are homologous to the     ( x i ) SEQUENCE DESCRIPTION: SEQ ID NO:1:

Glx   Xaa   Gln   Leu   Arg   Glu   Ser   Gly   Pro   Ser   Leu   Val   Lys   Thr
1                           5                             10

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( D ) TOPOLOGY: linear     ( i i ) MOLECULE TYPE: peptide     ( i i i ) HYPOTHETICAL: NO     ( v ) FRAGMENT TYPE: N-terminal     ( v i ) ORIGINAL SOURCE:
        ( A ) ORGANISM: Mus musculus     ( i x ) FEATURE:
        ( A ) NAME/KEY: Peptide
        ( B ) LOCATION: 1..15
        ( D ) OTHER INFORMATION: /label=peptide
            / note="amino terminal sequence of a murine IgM heavy chain polypeptide"

( i x ) FEATURE:
        ( A ) NAME/KEY: Peptide
        ( B ) LOCATION: 3..13
        ( D ) OTHER INFORMATION: /label=peptide
            / note="region homologous to amino terminus of B. burgdorferi 83 kDA prote..."

( x i ) SEQUENCE DESCRIPTION: SEQ ID NO:2:

```
Glu Val Gln Leu Gln Glu Ser Gly Pro Ser Leu Val Lys Pro Ser
 1               5                  10                  15
```